US 8,840,545 B2
Sep. 23, 2014

(12) United States Patent
Watanabe

(54) ENDOSCOPE

(75) Inventor: Katsushi Watanabe, Hachioji (JP)

(73) Assignee: Olympus Medical Systems Corp. (JP)

( * ) Notice: Subject to any disclaimer, the term of this patent is extended or adjusted under 35 U.S.C. 154(b) by 1382 days.

(21) Appl. No.: 12/180,939

(22) Filed: Jul. 28, 2008

(65) Prior Publication Data
US 2009/0036742 A1 Feb. 5, 2009

(30) Foreign Application Priority Data
Aug. 3, 2007 (JP) ................................ 2007-202804

(51) Int. Cl.
A61B 1/06 (2006.01)
A61B 1/00 (2006.01)
A61B 1/04 (2006.01)
A61B 1/005 (2006.01)
A61B 1/07 (2006.01)
A61B 1/12 (2006.01)

(52) U.S. Cl.
CPC .............. *A61B 1/00052* (2013.01); *A61B 1/042* (2013.01); *A61B 1/0684* (2013.01); *A61B 1/0052* (2013.01); *A61B 1/0057* (2013.01); *A61B 1/07* (2013.01); *A61B 1/12* (2013.01)
USPC .......................................... 600/178; 600/177

(58) Field of Classification Search
USPC .......... 600/154, 178–179, 177, 180, 181, 182
See application file for complete search history.

(56) References Cited

U.S. PATENT DOCUMENTS

| 4,874,364 A * | 10/1989 | Morris et al. .................... 604/35 |
| 5,634,711 A | 6/1997 | Kennedy et al. .............. 362/119 |
| 5,865,727 A * | 2/1999 | Sano et al. ..................... 600/178 |
| 6,932,599 B1 | 8/2005 | Hartung .......................... 433/29 |
| 7,896,526 B2 * | 3/2011 | Irion et al. ..................... 362/294 |
| 2005/0156186 A1 | 7/2005 | Lin et al. ........................ 257/99 |
| 2006/0085969 A1 | 4/2006 | Bennett et al. .................. 29/600 |
| 2006/0116553 A1 * | 6/2006 | Dunki-Jacobs et al. ...... 600/179 |

FOREIGN PATENT DOCUMENTS

| EP | 1 875 853 A1 | 1/2008 |
| JP | 63-502728 | 10/1988 |
| JP | 02-200234 | 8/1990 |
| JP | 06-315455 | 11/1994 |
| JP | 9-122065 | 5/1997 |

(Continued)

OTHER PUBLICATIONS

European Search Report dated Oct. 30, 2008.
Office Action issued by the Japanese Patent Office on Nov. 1, 2011 in connection with corresponding Japanese Patent Application No. 2007-202804.
Translation of Office Action issued by the Japanese Patent Office on Nov. 1, 2011 in connection with corresponding Japanese Patent Application No. 2007-202804.

(Continued)

Primary Examiner — Alireza Nia
(74) Attorney, Agent, or Firm — Ostrolenk Faber LLP

(57) ABSTRACT

An endoscope includes an insertion portion which is to be inserted into a subject, and an operation portion which is connected to a proximal end of the insertion portion, and held by a user. A light source is provided in the operation portion. A heat transmission frame is provided with the light source in the operation portion, is able to transmit heat generated by the light source, and is at least partially electrically insulated. An external heat radiation part is connected to the heat transmission frame, is at least partially exposed to the outside of the operation portion, and radiates heat transmitted to the heat transmission frame to the outside of the operation portion.

13 Claims, 9 Drawing Sheets

(56) References Cited

FOREIGN PATENT DOCUMENTS

| | | |
|---|---|---|
| JP | 2001-144447 | 5/2001 |
| JP | 2002-0348891 | 2/2002 |
| JP | 2003-010097 | 1/2003 |
| JP | 2005-329173 | 12/2005 |
| JP | 2006-346197 | 12/2006 |
| JP | 2007-044350 | 2/2007 |
| WO | WO 2006-046559 | 5/2006 |

OTHER PUBLICATIONS

Office Action issued by the Japanese Patent Office on Feb. 28, 2012 in connection with corresponding Japanese Patent Application No. 2007-202804.

Translation of Office Action issued by the Japanese Patent Office on Feb. 28, 2012 in connection with corresponding Japanese Patent Application No. 2007-202804.

* cited by examiner

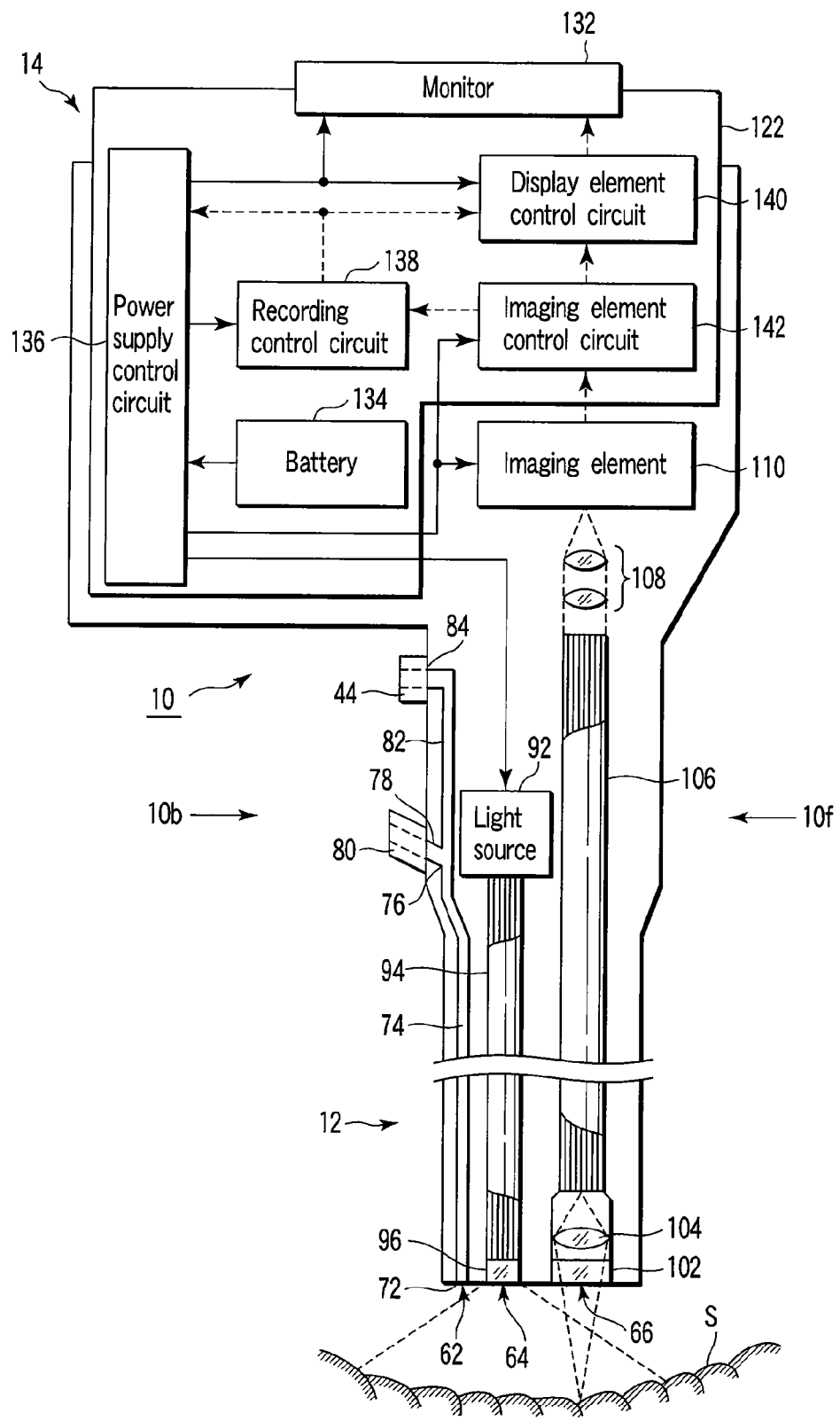
F I G. 2

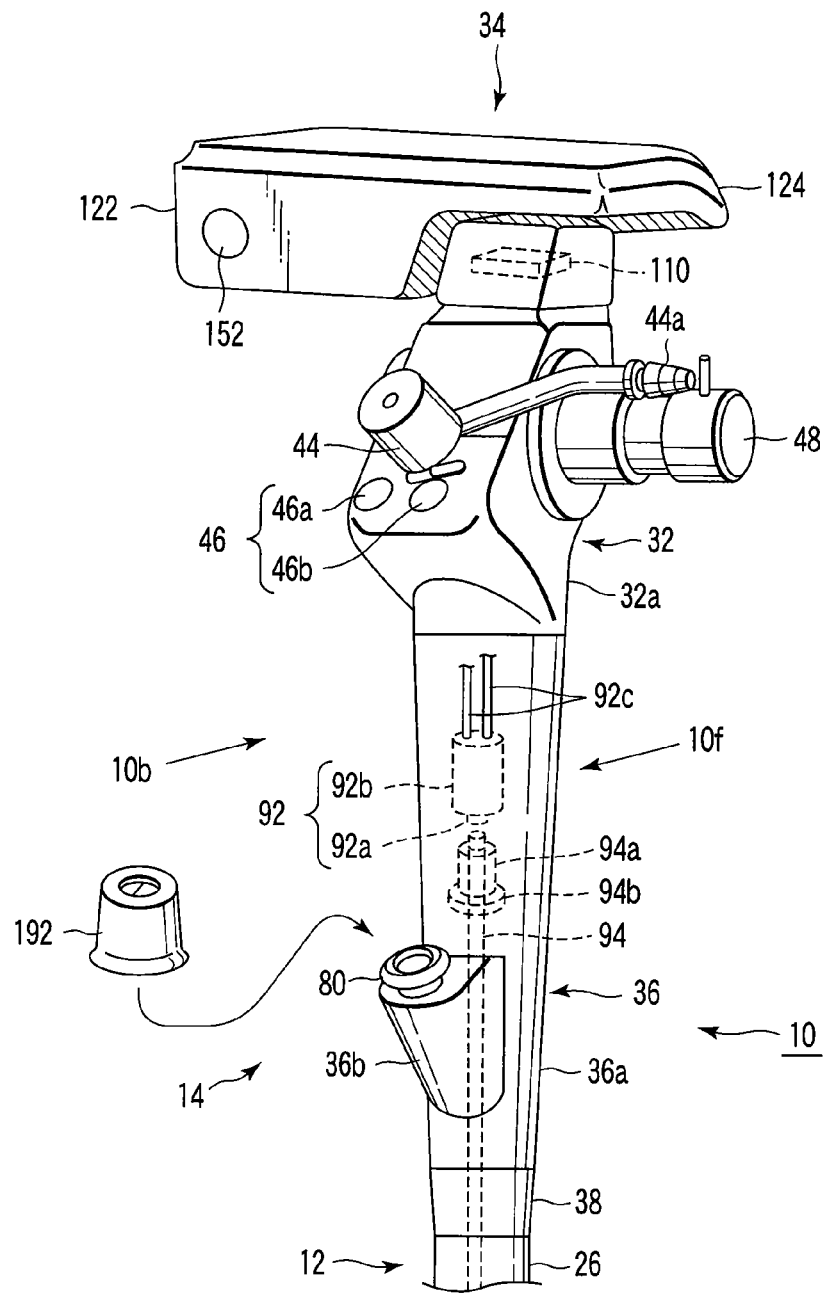
F I G. 4

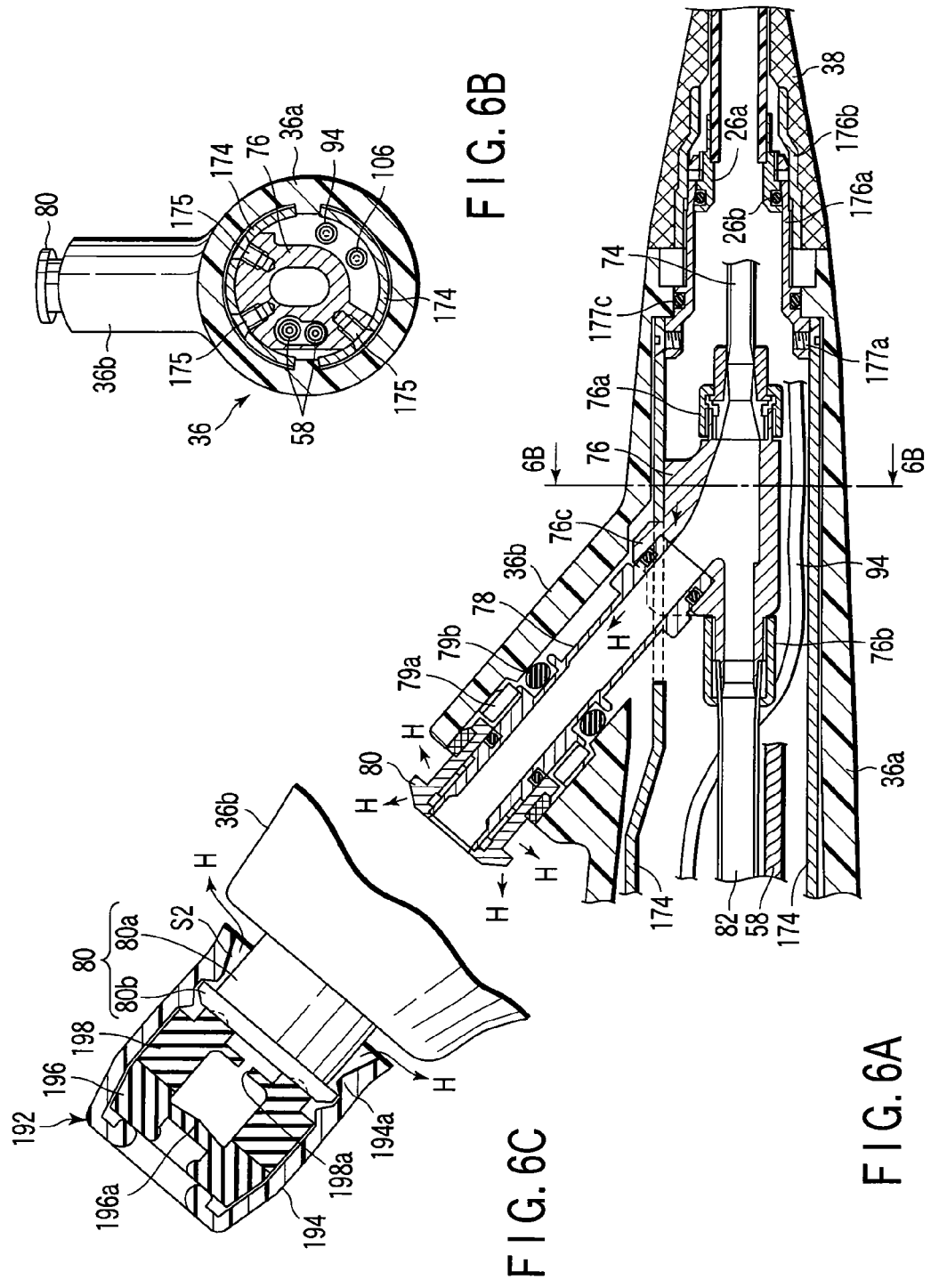

ENDOSCOPE

CROSS-REFERENCE TO RELATED APPLICATIONS

This application is based upon and claims the benefit of priority from prior Japanese Patent Application No. 2007-202804, filed Aug. 3, 2007, the entire contents of which are incorporated herein by reference.

BACKGROUND OF THE INVENTION

1. Field of the Invention

The present invention relates to an endoscope for a widespread use for various purposes.

2. Description of the Related Art

In a conventional endoscope, a light source is usually a peripheral device to be connected to an endoscope. Namely, a light source is provided separately from an endoscope. In recent years, an endoscope is combined with a peripheral device, and an LED is built into an endoscope for saving power and simplifying the structure (reducing the size) of the whole endoscope apparatus. In this case, the LED is provided at a distal end portion of an insertion portion of the endoscope, and directly illuminates an object area, or the LED is built into an operation portion, and its light is guided to a distal end portion of an insertion portion through a light guide fiber. In the former case, the distal end portion of the insertion portion needs to be made relatively large owing to dimensional restrictions, or to effectively diffuse heat generated from the LED.

However, in a medical endoscope, a distal end portion of an insertion portion needs to be as small as possible in order to minimize the discomfort experienced by the patient. In this case, an LED is built into an operation portion (as in the later case). In this case, an outer casing of the operation portion of the endoscope is constructed to be watertight, and resistant to chemicals by using engineering plastics. This also reduces the weight. Thus, the LED is built into the operation portion enclosed with plastic with low thermal conductivity, which makes it difficult to radiate heat generated by the LED to the outside.

When a surface temperature of the operation portion held by an operator is increased by the light emitted from the LED, this is unpleasant for the operator. Therefore, it is preferable to prevent conduction of heat from the LED to a grip part of the operation portion. On the other hand, it is necessary to radiate heat emitted from the LED to prevent a decrease in the light-emitting efficiency of the LED, and to prevent a reduction of the life of the LED.

Jpn. Pat. Appln. KOKAI Publication No. H9-122065 discloses a structure to effectively radiate heat generated by a light-emitting element provided in an operation portion to the outside, by transmitting heat to a heat radiation part exposed to the outside surface of an operation portion by using a heat pump.

BRIEF SUMMARY OF THE INVENTION

According to a first aspect of the present invention, there is provided an endoscope including:

an insertion portion to be inserted into a subject;

an operation portion which is connected to a proximal end of the insertion portion, and held by a user;

a light source provided in the operation portion;

a heat transmission frame which is at least partially electrically insulated, the heat transmission frame provided with the light source in the operation portion, and being able to transmit heat generated by the light source; and an external heat radiation part which is connected to the heat transmission frame, at least partially exposed to the outside of the operation portion, and radiates heat transmitted to the heat transmission frame to the outside of the operation portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic diagram showing the configuration of the inside (a channel, an illumination optical system, and an observation optical system) of the endoscope according to the first embodiment;

FIG. 4 is a diagrammatic perspective showing an operation portion of the endoscope according to the first embodiment;

FIG. 6A is a diagrammatic longitudinal cross section showing the grip part of the operation portion and a protection hood of the endoscope according to the first embodiment;

FIG. 6B is a diagrammatic transverse cross section along lines 6B-6B in FIG. 6A;

FIG. 6C is a diagrammatic partial cross section showing the state that a forceps plug is fitted to a treatment device insertion port provided in the grip part shown in FIG. 6A;

DETAILED DESCRIPTION OF THE INVENTION

Hereinafter, embodiments of the present invention will be explained with reference to the accompanying drawings. In the embodiments explained hereinafter, an endoscope is a medical endoscope with excellent transportability, which has an image display device built in an operation portion as one piece, and is applicable not only to a medical field, but other industrial fields.

[Embodiment 1]

First, a first embodiment will be explained by using FIG. 1A to FIG. 7.

Figures 1A, 1B:
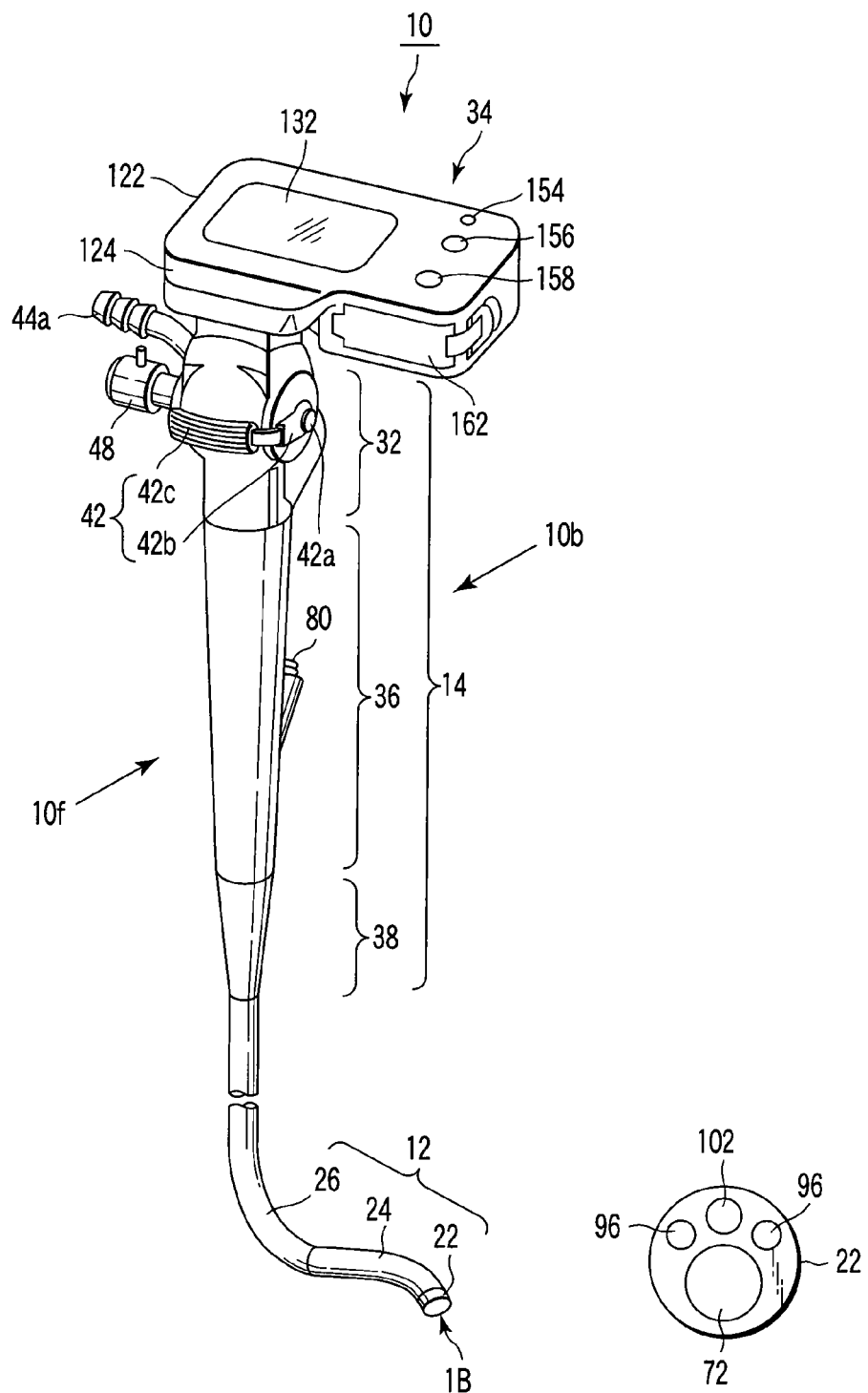
FIG. 1A is a diagrammatic perspective showing an endoscope according to a first embodiment of the invention.
FIG. 1B is a diagrammatic front view showing the part indicated by a reference number 1B in FIG. 1A.

As shown in FIG. 1A and FIG. 2, an endoscope 10 mainly includes an insertion portion 12 to be inserted into an observing area as a subject in the abdominal cavity, and an operation portion 14 connected to a proximal end of the insertion portion 12.

As shown in FIG. 1A, the insertion portion 12 mainly includes a hard distal end portion 22 provided at a distal end side of the insertion portion 12, a bending portion 24 connected to a proximal end side of the hard distal end portion 22, and a flexible portion 26 formed elongated shape and connected to a proximal end side of the bending portion 24. The proximal end of the flexible portion 26 is connected to the operation portion 14.

A base material of the hard distal end portion 22 is metal, for example, and the outside surface of the base material is covered with an insulation coating. Bending pieces of the bending portion 24 and a cylindrical braid covering the outside surface of the bending pieces are made of a metallic material, for example. The outside surfaces of the bending pieces and braid are covered with thin insulation rubber. A helicoidal pipe of the flexible portion 26 is made of a metallic material, for example, and the outside surface of the helicoidal pipe is covered with an insulation tube. The base material of the hard distal end portion 22 is connected to the foremost bending piece of the bending portion 24. The helicoidal pipe is connected to the rearmost bending pieces of the bending portion 24. An insulation tube made of PTFE is used for a channel tube 74 of a channel 62 described later, the channel tube 74 is inserted into the hard distal end portion, the bending pieces and the braid of the bending portion 24 and the helicoidal pipe of the flexible portion 26 of the insertion portion 12.

As shown in FIG. 1A and FIGS. 3 to 6C, the operation portion mainly includes an operation portion main body 32, an image display device 34 provided at an upper end of the operation portion main body 32, a grip part 36 connected to a lower end of the operation portion main body 32, and a protection hood 38 connected to a lower end of the grip part 36 to prevent buckling of the flexible portion 26.

Figure 3:
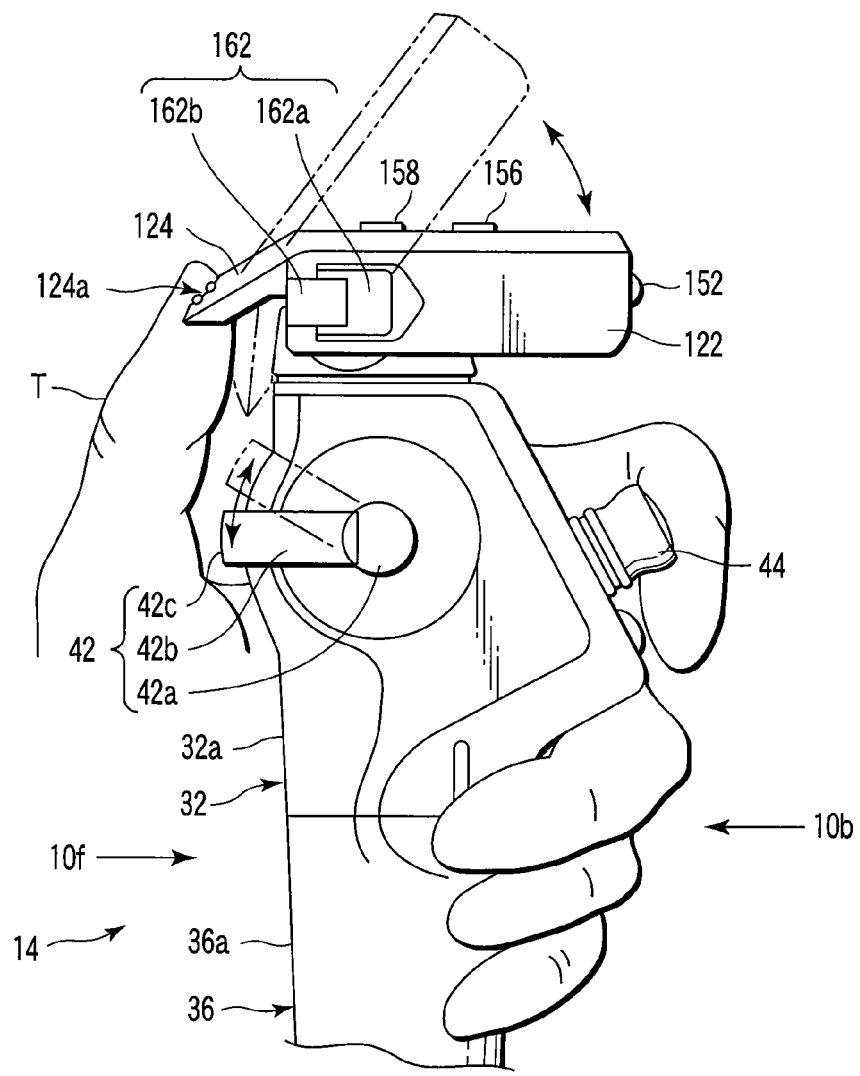
FIG. 3 is a schematic diagram showing the state that a grip part of an operation portion of the endoscope according to the first embodiment is held, and an image display device is inclined to a desired state.

The grip part 36 is provided between the operation portion main body 32 and insertion portion 12, and grasped by an operator for operating the endoscope 10. As shown in FIG. 3, the grip part 36 is shaped to be grasped by a thumb T and other fingers of the left-hand of an operator. The grip part 36 may be shaped to be grasped by the right-hand of an operator.

As shown in FIG. 1A, FIG. 3 and FIG. 4, the operation portion main body 32 is provided with a bending control lever 42, a suction button 44 having a suction port 44a, an image switch 46, and a vent port 48.

The bending control lever 42 is provided on the side (hereinafter called the front side) of the operation portion main body 32 indicated by the arrow 10f in FIG. 3. The suction button 44 and the image switch 46 are provided on the side (hereinafter called the rear side) of the operation portion main body 32 indicated by the arrow 10b in FIG. 4. The vent port 48 is provided on one side surface with respect to the front side 10f and rear side 10b.

As shown in FIG. 1A and FIG. 3, the bending control lever 42 includes a pivot 42a, an arm 42b, and a finger rest 42c. The pivot 42a penetrates the operation portion main body 32 in the horizontal direction in FIG. 1A (in the direction vertical to FIG. 3). The pivot 42a is provided on the other side with respect to the front side 10f and rear side 10b (the opposite side of the vent port 48). The pivot 42a is fixed to a pulley (not shown), on which operation wires 52 are wound in the operation portion main body 32. One end of the arm 42b is fixed to the pivot 42a. The other end of the arm 42b is connected to the finger rest 42c. The finger rest 42c is provided on the front side 10f close to the grip part 36, so as to be controlled by the thumb T of the left hand of the operator when grasping the grip part 36. Namely, the arm 42b and finger rest 42c of the bending control lever 42 are substantially L-shaped.

Figures 5A, 5B:
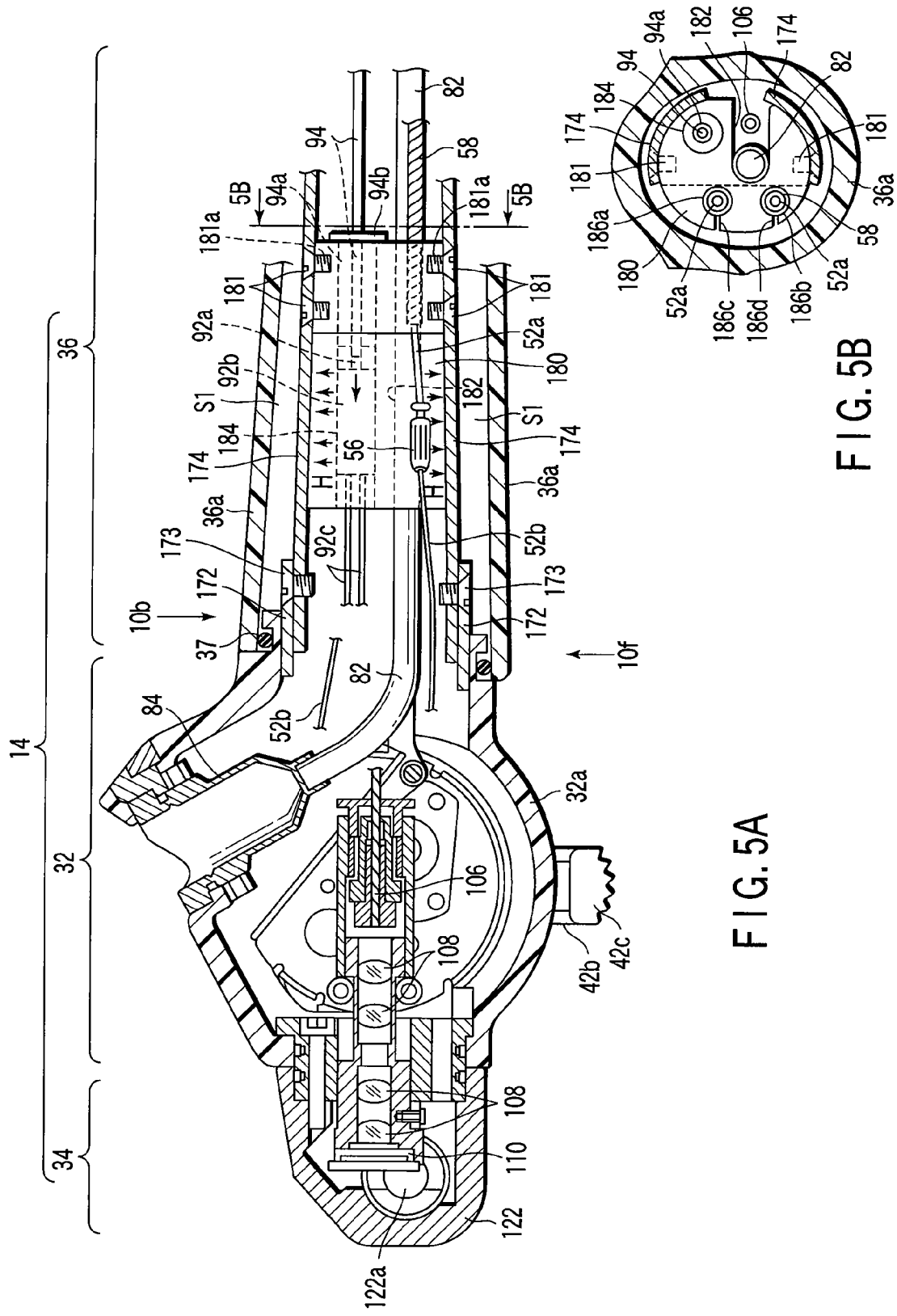
FIG. 5A is a diagrammatic longitudinal cross section showing an operation portion main body and the grip part of the operation portion of the endoscope according to the first embodiment.
FIG. 5B is a diagrammatic transverse cross section along lines 5B-5B in FIG. 5A.

As shown in FIG. 5A, a pair of operation wires 52 is connected in the grip part 36 of the operation portion 14 by a wire length adjuster 56, respectively. Namely, each operation wire 52 includes a first wire 52a and a second wire 52b.

A distal end of the first wire 52a is fixed to the not-shown foremost bending piece in the bending portion 24, or the hard distal end portion 22. A proximal end of the first wire 52a is extended to the inside of the grip part 36 of the operation portion 14 through the flexible portion 26 of the insertion portion 12.

One end of the second wire 52b is fixed to the pulley in the operation portion main body 32, and the other end is extended to the inside of the grip part 36. The first and second wires 52a and 52b are connected by the wire length adjuster 56, so that the wires 52a and 52b can be disconnected and the length of each wire 52a and 52b can be adjusted. Further, the first wire 52a is covered with a coil-shaped angle coil 58, in substantially the whole length of the protection hood 38 and flexible portion 26, except for the bending portion 24 and the part close to the wire length adjuster 56. This prevents friction between the first wire 52a and a fixing member 180 to be described later, and breakage of the first wire 52a when contacting other members, thereby protecting the first wire 52a.

The suction port 44a shown in FIG. 1A and FIG. 4 is connectable to a suction unit through a tube (both not shown). By operating the suction unit and suction button 44, the operator can suction bodily fluids and phlegm from the abdominal cavity through the channel 62 as a tubular member. The channel 62 is extended into the operation portion 14 and insertion section 12, so that one end (proximal end) is opened to the operation portion main body 32, and the other end (distal end) is opened to the distal end surface of the hard distal end portion 22.

The image switch 46 provided on the rear side 10b of the operation portion main body 32 includes an image recording switch 46a and an image reproducing switch 46b. The image recording switch 46a is turned on when recording an image displayed in a monitor 132, described later, of the image display device 34, on a recording medium connected to a recording control circuit 138 (refer to FIG. 2) described later. The image reproducing switch 46b is turned on when an image recorded on a recording medium is reproduced.

On the left side in FIG. 1A (on the right side in FIG. 4) of the operation portion main body 32, the vent port 48 is provided for supplying air into the insertion portion 12 and the operation portion 14 when checking the endoscope 10 for water leakage. A not-shown cap is removably fitted to the vent port 48 to open the inside of the endoscope 10 to the atmosphere to prevent the thin rubber covering the outside of the bending portion 24 from being broken under vacuum, when the endoscope 10 is left in vacuum for sterilization or transported by air.

As shown in FIG. 2, the insertion portion and the operation portion 14 of the endoscope 10 is provided with the channel 62, an illumination optical system 64, and an observation optical system 66.

The channel 62 includes an opening 72 of the hard distal end portion 22 of the insertion portion 12 (refer to FIG. 1B), a channel tube 74 connected to the opening 72 to insert the insertion portion 12 (refer to FIG. 6A), a branch part 76 as a heat transmission frame (refer to FIG. 6A), a connection tube 78 as a heat transmission frame (refer to FIG. 6A), a treatment device insertion port (opening) 80 as an external heat radiation part of the endoscope 10, a suction path 82 (refer to FIG. 5A and FIG. 6A), and a suction button housing 84 (refer to FIG. 5A). The suction button 44 having the suction port 44a (refer to FIG. 4) is fitted in the suction button housing 84.

The suction port 44a and treatment device insertion port 80 are communicated with each other inside the operation portion 14. Namely, the suction button housing 84 and the suction port 44a are communicated with the connection tube 78 and the treatment device insertion port 80 due to the suction path 82 and branch part 76.

The suction port 44a of the operation portion main body 32 is provided on the rear side 10b of the endoscope 10. The suction port 44a is used to suction bodily fluids and phlegm from the abdominal cavity. The treatment device insertion port 80 of the grip part 36 is provided on the rear side 10b of the endoscope 10. The treatment device insertion port 80 is used to insert/remove a treatment device into/from the abdominal cavity, by inserting/removing a treatment device such as forceps into/from the channel 62 (refer to FIG. 2).

As shown in FIGS. 6A to 6C, the branch part 76 includes a first connector 76a connected to the channel tube 74, a second connector 76b connected to the suction path 82, and a third connector 76c connected to the connection tube 78. A central axis of the first connector 76a is substantially same as a central axis of the second connector 76b. Further, the treatment device insertion port 80 is fixed to the connection tube 78 with a screw. Namely, the treatment device insertion port 80 and connection tube 78 are communicated with the suction button housing 84 through the branch part 76 and suction path 82 inside the operation portion 14.

The branch part 76, connection tube 78 and treatment device insertion port 80 are made of materials with good thermal conductivity, such as metal. The channel tube 74 and suction path 82 are made of a resin material such as PTFE with insulation, resistance to chemicals and resistance to heat.

As shown in FIG. 2, the illumination optical system 64 includes a light source 92, a light guide bundle 94, and an illumination window 96 (refer to FIG. 1B). The observation optical system 66 includes an observation window 102 (refer to FIG. 1B), an objective lens 104, an image guide 106, an image-forming lens 108, and an imaging element 110.

As shown in FIG. 1B, the illumination window 96 and the observation window 102 are fixed to the hard distal end portion 22. As shown in FIG. 2, at a proximal end side of the illumination window 96, a distal end of the light guide bundle 94 is fixed to the hard distal end portion 22. At a proximal end of the observation window 102, the objective lens 104 is fixed to the hard distal end portion 22. At a proximal end side of the objective lens 104, the distal end of the image guide 106 is fixed to the hard distal end portion 22. The light guide bundle 94 and image guide 106 are extended to the operation portion 14 through the bending portion 24 and flexible portion 26.

Figure 7:
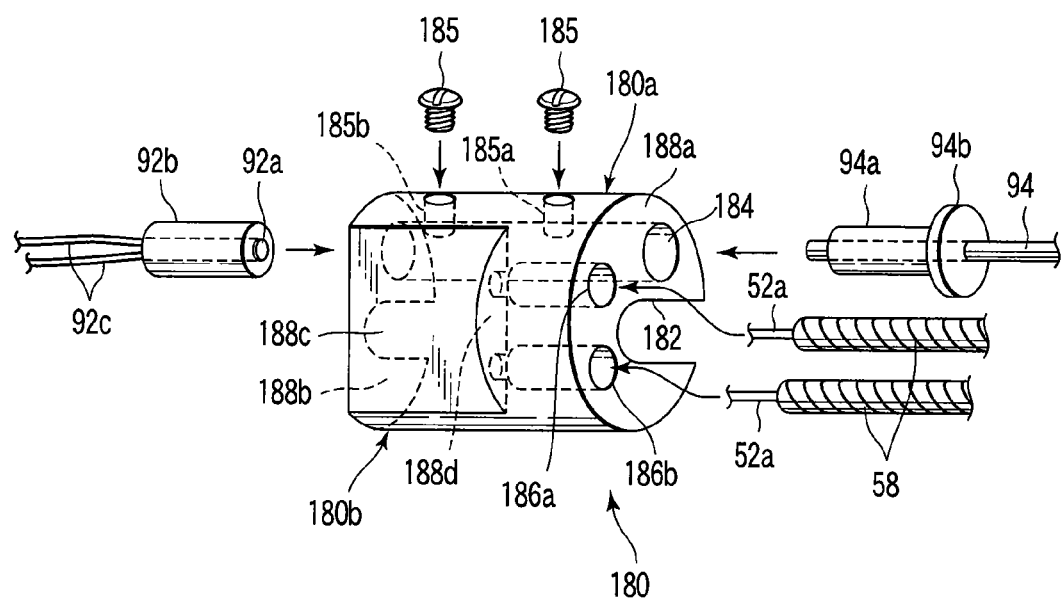
FIG. 7 is a diagrammatic perspective showing the state that a light guide bundle, a light source and an operation wire are arranged for a fixing member, which has electric insulation and good thermal conductivity, and is fixed to the inside of an operation portion of the endoscope according to the first embodiment.

In the light guide bundle 94, a number of light guide fibers are collected. A protection tube surrounds this bundle of parallel light guide fibers. As shown in FIG. 4, FIG. 5A and FIG. 7, a light guide connector 94a having a flange 94b is fixed to the proximal end of the light guide bundle 94.

The light source 92 is fixed to the inside of the operation portion 14. The light source 92 includes an LED 92a, an LED base 92b, and a lead wire 92c. The LED base 92b is shaped like an elongated cylinder with a small diameter, and is provided with the LED 92a on one end face. The lead wire 92c is extended from the other end face of the LED base 92b, and connected to a power supply control circuit 136 described later (refer to FIG. 2).

As shown in FIG. 4, the LED 92a is provided opposing the proximal end of the light guide bundle 94. At this time, the LED 92a, light guide bundle 94 and illumination window 96 are optically connected. Therefore, light from the LED 92a is emitted from the distal end of the insertion portion 12 through the light guide bundle 94 and illumination window 96.

As shown in FIG. 4 and FIG. 5A, the image-forming lens 108 and the imaging element 110 are fixed to the operation portion main body 32. The image-forming lens 108 is fixed to the proximal end of the image guide 106. The imaging element 110 is fixed at a position where the image-forming lens 108 forms an observation image. At this time, the observation window 102, objective lens 104, image guide 106, image-forming lens 108 and imaging element 110 are optically connected. Therefore, the light emitted from the illumination window 96 illuminates the subject S (refer to FIG. 2), the reflected light from the subject S is imaged by the imaging element 110 through the observation window 102, objective lens 104, image guide 106 and image-forming lens 108. Namely, an observation image can be obtained.

The imaging element 110 uses a CCD and CMOS, for example.

As shown in FIG. 1A and FIG. 2 to FIG. 4, the operation portion main body 32 is provided with the image display device 34. As shown in FIG. 1A, FIG. 3 and FIG. 4, the outside frame of the image display device 34 is formed by a main unit (cabinet) 122 shaped substantially as a rectangular parallelepiped (box-shape), and a tilt lever (a finger rest) 124 extended from a corner of one side of the main unit 122 to the front side 10f of the endoscope 10 in a plane. The main unit 122 and tilt lever 124 are formed as one piece. On the front surface of the main unit 122, a monitor 132 for displaying an endoscopic image is provided.

As shown in FIG. 1A and FIG. 3, the main unit 122 is pivotally supported by a pivot 122a shown in FIG. 5A at the upper end of the operation portion 14. Therefore, as shown in FIG. 3, the monitor 132 is movable at a desired angle between the direction of facing up with respect to the main operation portion 32 and the direction of facing to the front side 10f of the endoscope 10. Namely, the monitor 132 can be inclined to an easy-to-see position for a user. For example, it is preferable that the direction of forming the tilt lever 124 is on the front side 10f of the endoscope 10 (the position close to a user). In this case, the tilt lever 124 is operated by the ball of the thumb T of a left hand, for example, of an operator grasping the grip part 36. The upper surface of the tilt lever 124 is provided with slip stopper 124a as a plurality of protrusions.

Further, as shown in FIG. 2, the main unit 122 contains a battery 134, a power supply control circuit 136, a recording control circuit 138 having a recording medium such as an internal memory (not shown), a display element control circuit 140, and an imaging element control circuit 142 as a processing circuit.

The battery 134 is connected to the power supply control circuit 136. The power supply control circuit 136 is connected to the monitor 132, recording control circuit 138, display element control circuit 140, and imaging element control circuit 142. Further, the power supply control circuit 136 is also electrically connected to the light source 92 and imaging element 110, and supplies power to these parts.

The power supply control circuit 136 receives the power supplied from the battery 134, and outputs a suitable driving power to the light source 92, imaging element 110, monitor 132, recording control circuit 138, display element control circuit 140, and imaging element control circuit 142.

The power supply control circuit 136 includes a power switch 152, and is turned on/off by operating the power switch 152. The battery 134 employs a rechargeable secondary cell, which can be inserted into and removed from a slot of the housing, described later.

The recording control circuit 138 is supplied with signals from the image switch 46 provided in the operation portion main body 32 (refer to FIG. 4), and a still image recording changeover switch 156 and a moving image recording changeover switch 158 provided in the image display device 34 (refer to FIG. 1).

According to the input signals from these switches, the recording control circuit 138 controls recording, reproducing and suspending and so on of a signal of an endoscopic image as a still image or a moving image. Namely, the recording control circuit 138 stores an observation image of a subject area S signalized by the imaging element control circuit 142 on a recording medium, and outputs the stored signal to the display element control circuit 140 according to the instructions for reproducing and suspending and so on from the image reproducing switch 46b.

The recording control circuit 138 can contain an external recording medium such as an external recording element attachable to/detachable from the slot of the housing, to be described later, in addition to the internal memory described above.

The display element control circuit 140 visualizes a signal from the recording control circuit 138 or the imaging element control circuit 142, and displays an endoscopic image in the monitor 132. The recording control circuit 138 sends an instruction signal to the power supply control circuit 136 to supply power to the light source 92, imaging element 110 and imaging element control circuit 142, according to the signals input from the switches 46, 156 and 158.

As shown in FIG. 1A and FIG. 4, a power switch 152, a power indicator 154, a still image recording switch 156 and a moving image recording switch 158 are provided on the surface of the main unit 122, in addition to the monitor 132. Particularly, as shown in FIG. 4, the power switch 152 is provided on the rear side 10b of the main unit 122. The power indicator 154, still image recording changeover switch 156 and moving image recording changeover switch 158 are provided in the marginal area of the monitor 132, for example. The power switch 152 and power indicator 154 are connected to the power supply control circuit 136. Therefore, the power indicator 154 is continuously turned on since the power switch 152 is turned on, and turned off when the power is turned off.

The still image recording changeover switch 156 and moving image recording changeover switch 158 are connected to the recording control circuit 138. The still image recording changeover switch 156 is pressed to turn on when setting a still image for an endoscopic image to record. The moving image recording changeover switch 158 is pressed to turn on when setting a moving image for an endoscopic image to record.

The main unit 122 is provided with a housing (not shown), and a cover 162 configured to open and close the housing. The housing is provided with slots for housing the battery 134 and an external recording element (a storage medium) such as a not-shown memory card (e.g., an XD picture card (registered trademark), respectively. The external recording element can transfer data from the internal memory of the recording control circuit 138. The slot for housing the battery 134 is connected to the power supply control circuit 136, and the slot for housing the memory card is connected to the recording control circuit 138.

These components provided in the main unit 122 are constructed to be watertight. Particularly, the cover 162 to open/close the housing ensures the watertight structure of the housing of the main unit 122, with a fixed claw 162a and a buckle lever 162b.

In FIG. 1A, the power indicator 154, still image recording changeover switch 156, and moving image recording changeover switch 158 are placed apart from the tilt lever 124, but they may be provided between the upper surface of the tilt lever 124 and the marginal area of the monitor 132. In this case, an operator can operate the still image recording changeover switch 156 and moving image recording changeover switch 158 by the thumb of the hand grasping the grip part 36 of the endoscope 10.

An observation image of the subject area S taken by the imaging element 110 is output from the imaging element 110 to the imaging element control circuit 142. The imaging element control circuit 142 converts the observation image of the subject area S taken by the imaging element 110 to a signal, and outputs the signal to the recording control circuit 138 and display element control circuit 140.

Next, an explanation will be given on the structure to provide the light source 92 inside the operation portion 14, by referring to FIG. 5A to FIG. 7.

As shown in FIGS. 5A to 6C, the operation portion main body 32 and grip part 36 of the operation portion 14 are provided with outer casings 32a and 36a, respectively. These outer casings 32a and 36a are made of so-called engineering plastic (plastic material) with resistance to chemicals, resistance to heat, and insulation.

A sealing member 37 such as an O-ring is provided between the outside of the end portion of the outer casing 32a of the operation portion main body 32 and the inside of the proximal end portion of the outer casing 36a of the grip part 36, so that the outer casing 32a of the operation portion main body 32 and the outer casing 36a of the grip part 36 are fixed each other.

Therefore, the insides of the outer casings 32a and 36a are made watertight.

The outer casing 32a of the operation portion main body 32 is provided with the suction button housing 84 and the pivot 42a of the bending control lever 42.

The outer casing 36a of the grip part 36 is shaped cylindrical with a protection hood 38 fixed to the distal end (the insertion portion 12), and the proximal end (close to the operation portion main body 32) is fixed to the outer casing 32a of the operation portion main body 32. Further, the outer casing 36a of the grip part 36 is provided with a cylindrical extension 36b to house a connection tube 78 and treatment device insertion port 80.

A first frame (intermediate plate) 172 made of a metallic material such as aluminum is fixed to the inside of the outer casing 36a of the operation portion main body 32. A pair of second frames 174 made of metallic material with good thermal conductivity, such as aluminum is fixed to the inside of the first frame 172, as a heat transmission frame. The second frames 174 are provided inside the outer casing 36a of the grip part 36. Particularly, the second frames 174 are extended from the distal end (the insertion portion 12) of the grip part 36 to the proximal end (the operation portion main body 32), along the front side 10f and rear side 10b of the outer casing 36a. Namely, the second frame 174 is divided into two or more parts, for example a pair. The pair of second frames 174 is not limited to a symmetrical form, but is shaped in various forms to coincide with the shape of the outer casing 36a.

Each second frame 174 is fixed with a screw 173 to the first frame 172 fixed to the inside of the outer casing 32a of the operation portion main body 32. As shown in FIG. 6B, in the side of the second frame 174 close to the insertion portion 12, the branch part 76, at which the channel 62 and treatment device insertion port 80 are joined, is fixed tightly to the second frame 174 with a screw 175.

The suction path 82 of the channel 62, the image guide 106 of the observation optical system 66, bending operation wire 52, and the light guide bundle 94 of the illumination optical system 64 are extended in the space between the opposing second frames 174. The lead wire 92c extended from the power supply control circuit 136 to the LED base 92b is also extended to transmit the power supplied from the battery 134 to the light source 92.

As shown in FIGS. 5A and 5B, a light-emitting means fixing member (a light source fixing member) 180 as a heat transmission frame is fixed tightly to the inside surface of the second frame 174 with a screw 181 as a fixing member in the space of the opposing second frames 174. Namely, the fixing member 180 is fixed to the inside of the outer casing 36a of the grip part 36.

As shown in FIG. 6A, the second connector 76b of the branch part 76 is provided inside the second frame 174. The connection tube 78 is connected to the third connector 76c of the branch part 76 in being strongly pressed by the tightening force of a nut 79a to the inside surface of the extension 36b. The treatment device insertion port 80 is fixed to the connection tube 78 with a screw.

A sealing member 79b such as an O-ring is provided between the treatment device insertion port 80 and the extension 36b of the outer casing 36a so that there is a watertight configuration to keep out fluid therebetween.

At the distal end of the second frame 174, first and second connection members 176a and 176b are provided.

The first connection member 176a is connected to the second frame 174 with a screw 177a. The first connection member 176a connects the second frame 174 to the flexible portion 26 of the insertion portion 12. Namely, the inside surface of the first connection member 176a contacts the outside surface of a connector 26a at the proximal end of the flexible portion 26 of the insertion portion 12.

A sealing member 26b such as an O-ring is provided between the inside surface of the first connection member 176a and the outside surface of the connector 26a of the proximal end of the flexible portion 26 so that there is a watertight configuration to keep out fluid therebetween.

A sealing member 177c such as an O-ring is provided between the outer casing 36a and the first connection member 176a so that there is a watertight configuration to keep out fluid therebetween.

The protection hood 38 made of rubber is formed on the outside surface of the first connection member 176a as one piece. The outside of the first connection member 176a is screwed into the inside of the second connection member 176b.

The first frame 172, second frame 174, branch part 76, connection tube 78, treatment device insertion port 80, connection members 176a and 176b, and connector 26a of the flexible portion 26 are made of metallic materials with good thermal conductivity, such as aluminum. The members to serve as fluid flow paths denoted by the reference numbers 76, 78 and 80 (refer to FIG. 6A) may be made of metallic materials with resistance to corrosion, such as stainless steel.

A space $S_1$ is provided between the second frame 174 and the inside surface of the outer casing 36a of the grip part 36. The space $S_1$ gives heat insulation to prevent heat H in the first frame 172, second frame 174, branch part 76, connection tube 78, treatment device insertion port 80, connection members 176a and 176b, and connector 26a of the flexible portion 26, from transferring to the outside of the outer casing 36a.

As shown in FIG. 7, a light-emitting means fixing member 180 is formed in a solid substantially cylindrical member, for example. The fixing member 180 is made of a material with good thermal conductivity and electrical insulation, such as aluminum nitride. The fixing member 180 includes a U-shaped through hole (a recess) 182 cut off from the side of the fixing member 180, a through hole 184 for the illumination optical system, and through holes 186a and 186b for the operation wires. Namely, the fixing member 180 is provided with the through holes 182, 184, 186a and 186b along the axial direction of the insertion portion 12. The through hole 184 for the illumination optical system and through holes 186a and 186b for the operation wires are provided along the axial direction of the fixing member 180.

The through hole 182 forms a tubular member insertion hole, and is U-shapes toward substantially the center of the light-emitting means fixing member 180, as shown in FIG. 5B and FIG. 7. Namely, the through hole 182 is formed by removing the fixing member 180 from the side toward substantially the central axis.

In the through hole 182, at least a part of the outer periphery of the suction path 82 of the channel 62 extended into the grip part 36 is provided so as to closely contact to the inside surface of the through hole 182. Further, the through hole 182 is provided with an image guide 106 adjacent to the suction path 82.

The through hole 184 is formed in cylindrical shape. As shown in FIG. 5A, the through hole 184 provides space for a light-emitting means. The LED base 92b provided with the LED 92a and the light guide connector 94a fixed to the light guide bundle 94 are inserted into the through hole 184.

The light guide connector 94a is inserted into one end (the distal end) of the through hole 184. When the flange 94b of the light guide connector 94a contacts one end of the through hole 184, the parts are positioned. Namely, the light guide bundle 94 is positioned for the fixing member 180.

As shown in FIG. 7, the LED base 92b provided with the LED 92a is inserted into the other end (the proximal end) of the through hole 184, so as to abut the LED 92a against the light guide bundle 94. The LED base 92b is connected with the lead wire 92c for supplying power to the LED 92a. In this state, the light guide connector 94a and LED base 92b are fixed with a screw 185 from the side of the fixing member 180. Therefore, illumination light from the LED 92a incidents the light guide bundle 94.

The diameters of the through holes 186a and 186b for the operation wires are large in the distal end side of the insertion portion 12, and small in the side farther from the distal end of the insertion portion 12. Namely, the through holes 186a and 186b are provided with steps. In the through holes 186a and 186b provided with steps, the first wires 52a of the operation wire 52 covered with the angle coil 58 can be provided in the large diameter area of the distal end side, and the first wires 52a without the angle coil 58 can be provided in the small diameter area of the proximal end side.

The through holes 186a and 186b are provided with slits 186c and 186d between the outer periphery of the fixing member 180 and the through holes 186a and 186b. The widths of these slits 186c and 186d are set to permit insertion of the operation wires 52 (the first wire 52a) into the through holes 186a and 186b, but not to permit insertion of the angle coils 58. Namely, only the operation wires 52 can be inserted into and removed from the slits 186c and 186d.

Further, as shown in FIG. 7, in the fixing member 180, the proximal end sides of the through holes 186a and 186b are cut off. Namely, a part of the proximal end side of the cylindrical fixing member 180 is removed. In this part, a pair of wire length adjusting members 56 is provided.

For example, when removing the first wires 52a of the operation wires 52 from the fixing member 180, the angle coils 58 can be removed from the through holes 186a and 186b of the fixing member 180 toward the distal end side, and the first wires 52a of the operation wires 52 can be removed from the slits 186c and 186d.

As described above, the light-emitting means fixing member 180 is made of a material (e.g., aluminum nitride) with good thermal conductivity and electrical insulation. The fixing member 180 is fixed tightly to the second frame 174 with good thermal conductivity, such as aluminum. Concretely, the fixing member 180 is fixed to the second frame 174 with the screw 181.

The fixing member 180 integrally includes a cylindrical part 180a close to the distal end side of the insertion portion 12, and a D-shaped part 180b close to the operation portion main body 32. One end face 188a of the fixing member 180 is formed in the cylindrical part 180a. The other end face 188b of the fixing member 180 is formed in the D-shaped part 180b. A plane part 188c is formed in the D-shaped part 180b. Further, a D-shaped end face 188d is formed in the boundary between the cylindrical part 180a and D-shaped part 180b.

As shown in FIG. 5A, the cylindrical part 180a is provided with four screw holes 181a to insert the screw 181. As shown in FIG. 7, the cylindrical part 180a is provided with a screw hole 185a to insert the screw 185 to fix the light guide connector 94a, and the D-shaped part 180b is provided with a screw hole 185b to insert the screw 185 to fix the LED base 92b.

The first connector 76a of the branch part 76 is connected to the proximal end of the channel tube 74 that is inserted into the insertion tube 12 and opened at the distal end of the insertion portion 12.

The treatment device insertion port 80 includes a cylindrical part (opening) 80a exposed to the outside from the extension 36b of the outer casing 36a in the part exceeding the area to be held by an operator (near the proximal end of the insertion portion 12). This cylindrical part 80a is a part to radiate heat to the outside.

A flange 80b is formed projecting outward at the end portion of the cylindrical part 80a of the treatment device insertion port 80. A forceps plug 192 is attachable to and detachable from the treatment device insertion port 80, as shown in FIG. 6C.

As shown in FIG. 6C, the forceps plug 192 includes a cylindrical outer casing 194, and first and second rubber valves (valve elements) 196 and 198 provided inside the outer casing 194. The outer casing 194 and the first and second rubber valves 196 and 198 are made of insulation materials.

The first and second rubber valves 196 and 198 are provided in being overlapped in the outer casing 194. The first rubber valve 196 is made to contact the distal end of the outer casing 194. The first rubber valve 196 has a slit 196a. The second rubber valve 198 is provided with a circular opening 198a, for example to insert a treatment device (not shown). When a treatment device is not inserted, ends of the slit 196a of the first rubber valve 196 are abutted, and the inside of the forceps plug 192 is hermetically sealed. When a treatment device is inserted, the inside edge of the opening 198a of the second rubber valve 198 surely contact with the treatment device, and the inside of the forceps 192 is hermetically sealed.

The outer casing 194 of the forceps plug 192 can engage with the flange 80b of the treatment device insertion port 80. The proximal end portion of the outer casing 194 is shaped like a flare. Namely, the end portion of the cylindrical main body of the outer casing 194 is enlarged. Therefore, a clearance $S_2$ is provided between the treatment device insertion port 80 and the internal surface of the proximal end portion of the outer casing 194 of the forceps plug 192. The clearance $S_2$ radiates heat H transmitted to the treatment device insertion port 80.

When the forceps plug 192 is fitted to the treatment device insertion port 80, a projection 194a of the inside surface of the plastic outer casing 194 of the forceps plug 192 is elastically deformed, and the forceps plug 192 is pushed in until riding over the flange 80b of the treatment device insertion port 80. As shown in FIG. 6C, when the forceps plug 192 is completely fitted to the treatment device insertion port 80, the inside of the path is closed to the outside (outside air) with the two rubber valves 196 and 198.

When a forceps et al. is inserted into the channel tube 74, the distal end of the forceps is inserted into the slit (entrance) 196a of the first rubber valve 196 of the forceps plug 192, and inserted further while deforming by closely contacting the inside edge of the opening 198a of the second rubber valve 198.

Even after the forceps plug 192 is completely fitted to the treatment device insertion port 80, the end portion of the outer casing 194 of the forceps plug 192 does not contact the extension 36b of the outer casing 36a of the grip part 36, and the connection of the cylindrical part 80a of the treatment device insertion port 80 to the outside is ensured. Namely, the clearance $S_2$ is ensured.

Next, an explanation will be given on the function of the endoscope 10 configured according to the embodiment. In particular, an explanation will be given on a method of radiating heat H generated from the light source 92 provided in the operation portion 14.

First, in the state that the fixing member 180 is fixed to the second frame 174, the channel 62, illumination optical system 64 and observation optical system 66 are all provided in the fixing member 180. In this state, the channel 62, illumination optical system 64 and observation optical system 66 are guided to the distal end side of the insertion portion 12 or the operation portion main body 32 of the operation portion 14. Therefore, the endoscope 10 can be used in the state that the channel 62, illumination optical system 64 and observation optical system 66 inside the operation portion 14 are stably positioned.

Then, the power switch 152 of the endoscope 10 is turned on in the above state. When the power switch 152 is turned on, the endoscope 10 is supplied with power from the battery 134 of the image display device 34 through the power supply control circuit 136.

When the image display device 34 is set in the still image recording standby state, power is supplied from the power supply control circuit 136 to the LED base 92b provided in the grip part 36 of the operation portion 14 through the lead wire 92c, and power is also supplied to the imaging element 110.

When the power is supplied from the battery 134 through the power control circuit 136, the LED 92a emits an illumination light. The illumination light emitted from the LED 92a is incident to the proximal end of the light guide bundle 94, guided to the distal end of the light guide bundle 94, and emitted through the illumination window 96 provided at the distal end of the light guide bundle 94, thereby a desired part of the subject area S in the abdominal cavity is illuminated.

Reflected light from the illuminated subject area S by the illumination light forms an observation image through the observation window 102 and objective lens 104 provided in the hard distal end portion 22. The observation image is incident to the other end of the image guide 106, and transmitted to one end of the image guide 106. Then, the observation image formed by the reflected light is imaged on the imaging element 110 through the image-forming lens 108 provided in the operation portion main body 32. Therefore, the observation image is imaged by the imaging element 110 controlled by the imaging element control circuit 142.

The observation image is transmitted from the imaging element 110 to the imaging element control circuit 142, display element control circuit 140 and monitor 132, and displayed real time in the monitor 132.

When a still image is recorded in this state, the image recording switch 46a on the rear side 10b of the operation portion main body 32 is turned on by an operator. Then, an image signal output from the imaging element control circuit 142 is recorded as a still image in an internal memory of the recording control circuit 138. Thereafter, when the image reproducing switch 46b on the rear side 10b of the operation portion main body 32 is pressed by an operator, the image data in the internal memory is output from the recording control circuit 138 to the display element control circuit 140, and displayed in the monitor 132. Then, when the image reproducing switch 46b is pressed, an image under observation is displayed in the monitor 132, instead of the display of a still image. Namely, an image under observation is displayed in real time in the monitor 132.

When an operator turns on the moving image recording switch 158 provided in the marginal area of the monitor 132 of the image display device 34, the still image recording standby state is switched to a moving image recording standby state. In this case, also, an observation image is transmitted from the imaging element 110 to the imaging element control circuit 142, display element control circuit 140 and monitor 132, and displayed in real time in the monitor 132.

When a moving image is recorded in this state, the operator turns on the image recording switch 46a on the rear side 10b of the operation portion main body 32. Then, a moving image is recorded in the internal memory of the recording control circuit 138 as described above.

While a moving image is being recorded, an image signal is output in real time to the display element control circuit 140 by one of the imaging element control circuit 142 and recording control circuit 138, and an observation image is displayed real time in the monitor 132.

Thereafter, when the image recording switch 46a is pressed again by an operator to turn off image recording, the recording is stopped. To reproduce a recorded moving image, the operator turns on the image reproducing switch 46b. Then, reproduction of a moving image is controlled as in the case of a still image. At the end of reproducing a moving image, the same control as at the end of reproducing a still image is performed, and the operation is returned to the state at the startup time.

The data recorded in the internal memory of the recording control circuit 138 can be transferred to the above-mentioned external storage element.

As an observation image of the endoscope 10 is continuously displayed in the monitor 132, the LED 92a continuously emits light. Thus, the LED 92a is heated.

Then, heat H generated from the LED 92a is transmitted to the LED base 92b. The fixing member 180 to which the LED base 92b is fixed is made of a material with good thermal conductivity, such as aluminum nitride. Therefore, heat H generated from the LED 92a is transmitted to the fixing material 180 through the LED base 92b.

The fixing member 180 tightly contacts the metallic second frame 174 with good thermal conductivity. Therefore, heat H generated from the LED 92a is transmitted further from the fixing member 180 to the second frame 174. Similarly, the metallic branch part 76 with good thermal conductivity is fixed to the distal end of the second frame 174. Therefore, heat H generated from the LED 92a is transmitted from the second frame 174 to the branch part 76.

The branch part 76 tightly contacts the metallic connection tube 78 with good thermal conductivity. Therefore, heat H generated from the LED 92a is transmitted from the branch part 76 to the connection tube 78. The connection tube 78 is tightly screwed into the metallic treatment device insertion port 80 with good thermal conductivity. Therefore, heat H generated from the LED 92a is transmitted from the connection tube 78 to the treatment device insertion port 80.

The treatment device insertion port 80 is provided on the outside of the endoscope 10. Therefore, the treatment device insertion port 80 is opened to outside air, and heat H generated from the LED 92a is radiated to the outside of the endoscope 10. In this way, heat H generated from the LED 92a is radiated.

Even if the forceps plug 192 is fitted to the treatment device insertion port 80, the clearance $S_2$ is made between the treatment device insertion port 80 and the outer casing 194 of the forceps plug 192. Therefore, the effect of radiating heat H is unchanged.

Further, since heat H generated from the LED 92a is radiated through the fixing member 180, second frame 174, branch part 76, connection tube 78 and treatment device insertion port 80, the amount of heat transmitted from the LED 92a in the grip part 36 of the operation portion 14 to the first frame 172 through the fixing member 180 and second frame 174 is decreased. This prevents heating of the outer casing 32a of the operation portion main body 32 and the outer casing 36a of the grip part 36, to which the first frame 172 is fixed.

Further, as the space $S_1$ is provided between the second frame 174 and the outer casing 36a of the grip part 36, heat H is not transmitted directly from the second frame 174 to the outer casing 36a, and the outer casing 36a of the grip part 36 is prevented from being heated.

If static electricity should occur at the metallic treatment device insertion port 80 for some reason, the static electricity flows in the treatment device insertion port 80, connection tube 78, branch part 76, second frame 174 and first frame 172, which are all made of metallic materials. However, the fixing member 180 is electrically insulated, and therefore does not allow the static electricity to flow through. Therefore, the static electricity does not flow to the LED 92a and LED base 92b. This prevents flow of the static electricity from the LED base 92b to the power supply control circuit 136 through the lead wire 92c. Further, the static electricity does not flow to the battery 134, recording control circuit 138, imaging element control circuit 142, display element control circuit 140, and imaging element 110 and so forth, which are connected to the power supply control circuit 136.

It is assumed that a high frequency treatment device (not shown) is inserted into the treatment insertion port 80 through the opening 72 of the hard distal end portion 22 of the insertion portion 12. At this time, if the device is erroneously operated, a high frequency current may flow in the metallic base material of the hard distal end portion 22, the metallic bending pieces and braid of the bending portion 24, and the metallic helicoidal pipe of the flexible portion 26 and so forth. In this case, the high frequency current may flow in the second frame 174. However, the fixing member 180 is electrically insulated, and therefore does not allow the high frequency current to flow through it. Therefore, the high frequency current does not flow to the LED 92a and LED base 92b. This prevents flow of the high frequency current in the power supply control circuit 136 through the lead wire 92c. Further, the high frequency current does not flow in the battery 134, recording control circuit 138, imaging element control circuit 142, display element control circuit 140, and imaging element 110 and so forth, which are connected to the power supply control circuit 136.

Therefore, the LED base 92b and LED 92a are securely protected against damage caused by static electricity and high frequency current. Further, the power supply control circuit 136 and so forth is completely protected against static electricity and high frequency current.

As explained above, the endoscope 10 according to the embodiment provides the following effects.

By fixing the fixing member 180 in the operation portion 14, the channel 62, illumination optical system 64 and observation optical system 66 can be stabilized when using the endoscope 10. This enables stable observation and treatment by using the endoscope 10.

Even if the LED 92a continuously emits light, heat H generated from the LED 92a can be radiated to the outside of the endoscope 10 through the LED base 92b, fixing member 180, second frame 174, branch part 76, connection tube 78, and treatment device insertion port 80, which are made of materials with good thermal conductivity.

Even if the forceps plug 192 is fitted to the treatment device insertion port 80, the clearance $S_2$ is ensured between the outer casing 194 of the forceps plug 192 and the treatment device insertion port 80, and a space (the clearance $S_2$) is provided between the outer casing 194 and the extension 36b of the grip part 36, heat H can be securely radiated from the treatment device insertion port 80 to the outside.

As describe above, heat H generated from the LED 92a can be radiated from a heat radiation part (the cylindrical part 80a of the treatment insertion port 80) to the outside, and the outer casing 32a of the operation portion main body 32 and the outer casing 36a of the grip part 36 grasped by an operator are positively heat insulated with the outer casings with low thermal conductivity. Therefore, an operator does not have an unpleasant heat sensation, caused be heating of the outer casing 32a of the operation portion main body 32 and the outer casing 36a of the grip part 36 by heat of the other parts. Namely, the operation portion 14 is able to prevent heat H from remaining therein in the heat generated from the LED 92a.

Further, as heat H generated from the LED 92a can be effectively radiated to the outside of the endoscope 10, a decrease in the light emission efficiency of the LED 92a can be effectively prevented, and the power consumption is reduced, and the life of the LED 92a is prolonged.

As the parts with good thermal conductivity and insulation are used in the heat transmission path from the LED 92a to the treatment device insertion port 80, resistance to static electricity from the outside and resistance to high frequency current can be ensured while maintaining the radiation effect. Namely, even if metallic parts are used for the frames 172 and 174 of the operation portion 14 to increase the radiation effect, a flow of static electricity and high frequency current into the LED 92a and electronic circuit parts can be prevented, and damage of these parts can be prevented.

The light-emitting means fixing member 180 including the LED base 92b adopts a material with good thermal conductivity and insulation, such as aluminum nitride, a flow of static electricity and high frequency current from the paths other than the treatment device insertion port 80 to the LED base 92b or other electric parts can be securely prevented.

In this case, by using the endoscope 10 with the insulating forceps plug 192 fitted to the treatment device insertion port 80, an operator is securely prevented from directly touching the metallic treatment device insertion port 80, for example. Therefore, an operator can be securely prevented from being influenced by a high frequency current.

In the embodiment explained herein, the bending portion 24 is bent in the vertical direction (two directions). However, it is also possible to bend in the horizontal direction.

In this case, it is preferable that the fixing member 180 be provided with two through holes parallel to the operation wire 52 through holes 186a and 186b, and the operation portion main body 32 be provided with another bending control lever (a control lever for bending in the horizontal direction).

According to the above first embodiment, the following can be said.

The operation portion 14 of the endoscope 10 includes the light source 92, heat transmission frame including an electrically insulated part (the branch part 76, connection tube 78, second frame 174 and fixing member 180), and the treatment device insertion port (opening) 80 connected to the heat transmission frame. And the treatment device insertion port 80 is partially exposed to the outside of the operation portion 14 and radiates heat H transmitted to the heat transmission frame to outside of the operation portion 14. The heat transmission frame (the branch part 76, connection tube 78, second frame 174 and fixing member 180) provides the light source 92 in the operation portion 14, and can transmit heat H generated from the light source 92. When the light source 92 in the operation portion 14 is heated, heat H of the light source 92 can be radiated to the outside of the endoscope 10 (the outside of the operation portion 14) by transmitting heat H to the heat transmission frame and treatment device insertion port 80. Therefore, the power consumption of the light source 92 is reduced, and the life of the light source 92 can prevent from having a short life. Further, as the branch part 76 and connection tube 78 are partially insulated, even if electric energy such as static electricity flows into the treatment device insertion port 80 and so forth, the electric energy is interrupted, and not transmitted to the light source 92. Therefore, the light source 92 is able to be securely prevented from being influenced by external electric energy. Therefore, even if electric energy such as static electricity is input, transmission of such electric energy to the light source 92 (e.g., LED 92a) and the substrate of the light source 92 through the heat transmission path is prevented, and both of the radiation effect and resistance to electric energy of the light source 92 can be ensured.

The operation portion 14 of the endoscope 10 described above includes the light source 92, heat transmission frame and treatment device insertion port 80. In addition, the heat transmission frame (the fixing member 180) has an insulating part to cover the light source 92 with an insulator. In this case, Since the fixing member 180 as an insulating part is provided around the light source 92, even if electric energy is input, transmission of the electric energy to the light source 92 through the heat transmission path is prevented, and both of the radiation effect and resistance to electric energy can be ensured.

The operation portion 14 of the endoscope 10 described above includes the light source 92, heat transmission frame (the fixing member 180) and treatment device insertion port 80, and further includes the channel 62 to connect the operation portion 14 and the hard distal end portion 22 of the insertion section 12. The treatment device insertion port 80 includes the cylindrical part 80a, forming the opening of the channel 62 in the operation portion 14, and the flange 80b. In this case, heat H of the light source 92 can be radiated from the cylindrical part 80a of the channel 62 and flange 80b, to the outside of the endoscope 10.

The forceps plug 192 having insulation can be attached to and detached from the cylindrical part 80a and flange 80b of the treatment device insertion port 80. The forceps plug 192 includes a substantially cylindrical outer casing 194 having a projection (an engaging part) 194a and first and second rubber valves (valve bodies) 196 and 198 provided in the outer casing 194. The outer casing 194 is attached to and detached from the cylindrical part 80a and flange 80b of the treatment device insertion port 80. The first and second rubber valves (valve bodies) 196 and 198 interrupt the flow of fluid from the inside of the channel 62 to the outside of the cylindrical part 80a and flange 80b of the treatment device insertion port 80. There is a clearance $S_2$ between the outer casing 194 of the forceps plug 192 and the cylindrical part 80a and flange 80b of the treatment device insertion port 80. In such a case, even if the forceps plug 192 is fitted to the cylindrical part 80a and flange 80b of the treatment device insertion port 80, there is a clearance $S_2$ between the forceps plug 192 and treatment device insertion port 80, and the cylindrical part 80a and flange 80b are exposed to the outside (outside air), and the heat H generated by the light source 92 can be radiated. Further, even if a high frequency current should flow in the metallic parts in the endoscope 10, the forceps plug 192, which is made of an insulation material, prevents the user of the endoscope 10 from directly touching the cylindrical part 80a and flange 80b. In this case, also, as described above, at least a part (the fixing member 180) of the heat transmission frame is electrically insulated, and even if electric energy such as a high frequency current flows into an external heat radiation part, such electric energy is interrupted, and is not transmitted to the light source 92. Therefore, the light source 92 is securely prevented from being influenced by external electric energy.

Of the outer casing 194 of the forceps plug 192, the end portion of the part close to the branch part 76 and connection tube 78 is enlarged with respect to the cylindrical part 80a and flange 80b of the treatment device insertion port 80. In this case, the clearance $S_2$ between the outer casing 194 of the forceps plug 192 and the cylindrical part 80a and flange 80b of the treatment device insertion port 80 can be made larger, and a higher radiation effect can be obtained.

The operation portion 14 includes the outer casing 36a on the outside of the transmission frame (the second frame 174).

The space $S_1$ is provided between the heat transmission frame and outer casing 36a. In this case, transmission of the heat H to the outer casing 36a of the operation portion 14 is prevented, the outer casing 36a is prevented from being heated, and the user therefore does not feel such heat.

The heat transmission frame (the second frame 174 and fixing member 180) is extended in the operation portion 14, from the side far from the light source 92 to the side close to the light source 92, with respect to the hard distal end portion 22 of the insertion portion 12. In this case, as the transmission frame is arranged in the operation portion 14 from the side far from the light source 92 to the side close to the light source 92, the operation portion 14 is able to have a desired strength, the heat transmission path is made longer, and heat H of the light source 92 can be transmitted to the treatment device insertion port 80 in the state diffused as much as possible. Therefore, heat H of the light source 92 (LED 92a) can be effectively radiated.

The transmission frame (the branch part 76, connection tube 78, second frame 174, and fixing member 180) provided with the operation portion 14 has an aluminum nitride member (the fixing member 180) having insulation and good thermal conductivity, in at least a part between the light source 92 and treatment device insertion port 80. In this case, the aluminum nitride member has insulation and good thermal conductivity, and even if electric energy occurs, transmission of such electric energy to the light source 92 through the heat transmission path is prevented by using the aluminum nitride member as a part of the heat transmission frame. This ensures both of a radiation effect and resistance to electric energy.

The heat transmission frame (the branch part 76, connection tube 78, second frame 174, and fixing member 180) includes a light source fixing member 180 having insulation and good thermal conductivity and provided with the light source 92, and a frame (the branch part 76, connection tube 78, and second frame 174) provided with the fixing member 180 and connected to the treatment device insertion port 80. In such a case, even if electric energy occurs, the light source fixing member 180 prevents transmission of such electric energy to the light source 92 through the heat transmission path, and ensures both of a radiation effect and resistance to electric energy.

The operation portion 14 includes the outer casing 36a, and the extension 36b provided in the outer casing 36a, on the outside of the frame (the branch part 76, connection tube 78, and second frame 174). The light source 92 includes LED the 92a. The treatment device insertion port 80 includes an opening of the channel 62 (the treatment device insertion port 80) in the extension 36b. In this case, when the LED 92a continuously emits light, the heat H of the LED 92a is transmitted from the branch part 76 and connection tube 78 to the opening of the channel 62 of an external heat radiation part, and radiated to the outside of the endoscope 10. At the same time, transmission of electric energy such as static electricity to the LED 92a is prevented, the power consumption is reduced, and the life of the LED 92a is prolonged. Namely, even if electric energy is generated, transmission of such electric energy to the LED 92a through the heat transmission path is prevented, and both of the radiation effect and resistance to electric energy of the LED 92 can be ensured.

The heat transmission frame (the second frame 174 and fixing member 180) is extended in the operation portion 14, from the side far from the light source 92 to the side close to the light source 92, with respect to the hard distal end portion 22 of the insertion portion 12. In this case, as the transmission frame is arranged in the operation portion 14 from the side far from the light source 92 to the side close to the light source 92, the operation portion 14 is given a desired strength, the heat transmission path is made longer, and heat H of the light source 92 can be transmitted to treatment device insertion port 80 in the state diffused as much as possible. Therefore, the heat H of the light source 92 (LED 92a) can be effectively radiated.

[Embodiment 2]

Hereinafter, an explanation will be given on a second embodiment by using FIG. 8A and FIG. 9. This embodiment is a modification of the first embodiment. The same members as in the first embodiment are given the same reference numbers, and a detailed explanation on these members will be omitted.

In the first embodiment described herein, the light-emitting means fixing member 180 is fixed to the second frame 174 by using the screw 181, and the light guide connector 94a and LED 92b are fixed to the light-emitting means fixing member 180 by using the screw 185. Further, the light-emitting means fixing member 180 is made of a material with thermal conductivity and electrical insulation, such as aluminum nitride.

Aluminum nitride is a ceramic. Ceramics are usually hard and brittle, and is difficult to tap (cut a thread) and costly. Further, even if tapping is possible, when the light-emitting means fixing member 180 is fixed to the second frame 174 with the screw 181, or when the light guide bundle 94 and LED base 92b are fixed to the light-emitting means fixing member 180 with the screw 185, the screw threads of the fixing member 180 may be broken when the screw (the fixing screw) is tightened to the light-emitting means fixing member 180. Thus, the screws 181 and 185 cannot be firmly tightened to the fixing member 180.

The screw 185 is used to fix the light guide connector 94a and LED 92b, having relatively small diameters and light weight, and need not be strongly tightened. In contrast, the screw 181 is tightened to the light-emitting means fixing member 180 having a large diameter, and the fixing strength and degree of contact need to be increased to ensure thermal conductivity between the parts. Thus, the screw 181 needs to be tightened by a stronger force. Therefore, the parts need to be assembled with consideration given to a screw tightening torque, particularly the screw 181, not to damage the screw hole 181a when the screw 181 is tightened. This decreases the assembly workability.

Figures 8A, 8B, 8C:
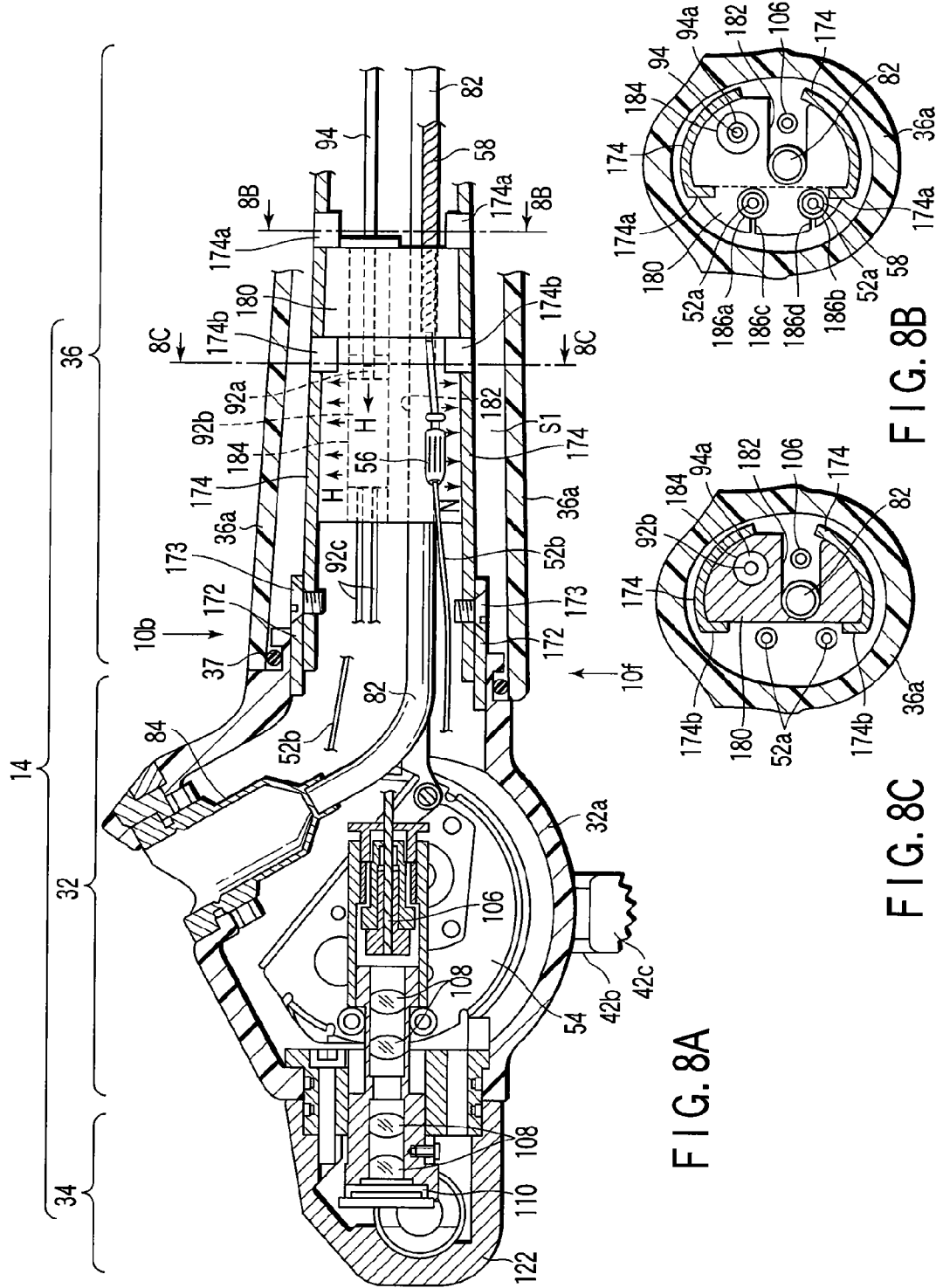
FIG. 8A is a diagrammatic longitudinal cross section showing a main body and a grip part of an operation portion of an endoscope according to a second embodiment.
FIG. 8B is a diagrammatic transverse cross section along lines 8B-8B in FIG. 8A.
FIG. 8C is a diagrammatic transverse cross section along lines 8C-8C in FIG. 8A.
Figure 9:
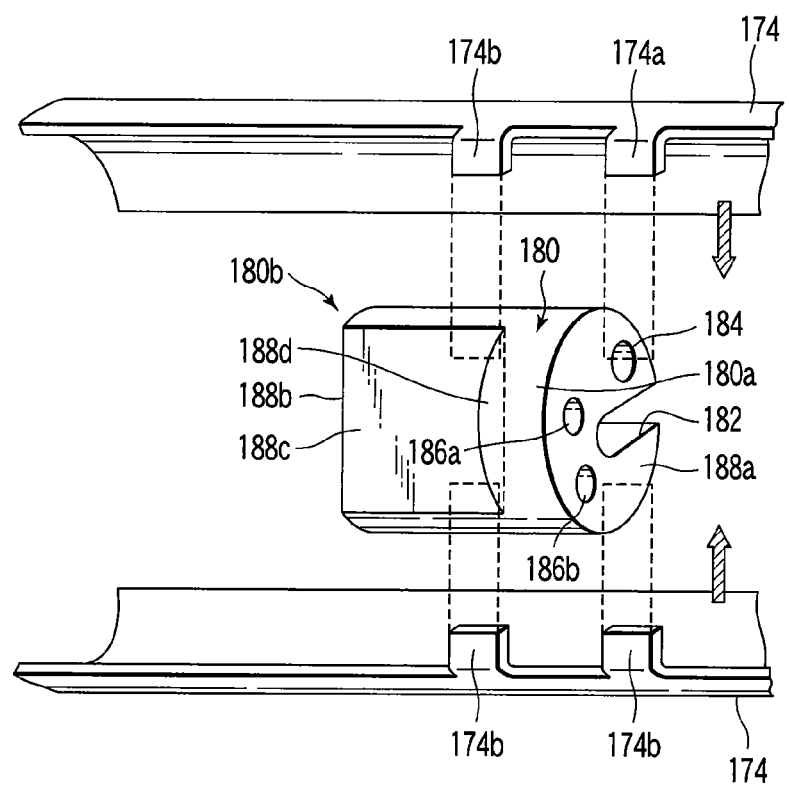
FIG. 9 is a diagrammatic perspective showing the state that a fixing member, which has electric insulation and good thermal conductivity, and is fixed to the inside of an operation portion of an endoscope according to a second embodiment, is engaged in the state fit tightly to a second frame having a pair of stopper lugs.

Therefore, in this embodiment, as shown in FIG. 8A to FIG. 9, a pair of second frames 174 made of metallic material such as aluminum is provided with stopper lugs 174a and 174b. The stopper lugs 174a and 174b are formed by projecting a part of the second frame 174, and bending this part substantially 90° inward.

The space between the stopper lugs 174a and 174b is substantially equal to the length of the cylindrical part 180a of the fixing member 180 (the length between one end face 188a and the D-shaped end face 188d). Therefore, when the fixing member 180 is held between the pair of second frames 174, the cylindrical part 180a of the fixing member 180 is positioned and fitted between the stopper lugs 174a and 174b of the cylindrical part 180a of the fixing member 180. Namely, in this assembled state, the side of the stopper lug 174a contacts one end face 188a of the cylindrical part 180a. The side of the stopper lug 174b is positioned in contact with the D-shaped end face 188a opposite to one end face 188a. Therefore, the fixing member 180 is positioned in the axial direction.

Further, the inside surface of the stopper lug 174b contacts the plane part 188c. Therefore, the fixing member 180 is uniquely positioned in the circumferential direction.

The screw (fixing screw) 181, which is used to fix the fixing member and second frame 174 in the first embodiment, is not used. Namely, the fixing member 180 is not provided with the screw hole 181a to insert the screw 181.

One end of the second frame 174 is fixed to the first frame 172 with the fixing screw 173. The other end of the second frame 174 is fixed to the branch part 76 with the screw 175 as shown in FIG. 6B, and fixed to the first connection tube 176a with the screw 177a.

The width of the space between second frames 174 is set to be slightly smaller than the outer dimensions of the light-emitting means fixing member 180. Therefore, in the assembled state, the second frames 174 are elastically deformed to tightly hold the fixing member 180.

The fixing member 180 and the light guide connector 94a of the light guide bundle 94 may be bonded with an adhesive with good thermal conductivity in the state that the flange 94b closely contacts one end face 188a of the fixing member 180. An adhesive with good thermal conductivity may be applied to the outside surface of the LED base 92b, and the LED 92a may be fixed to the light guide bundle 94 at a position where their proximal end portions closely contact each other. In this configuration, the screw 185 can be eliminated.

As explained herein, this embodiment provides the following effects.

As tapping is unnecessary for the fixing member 180, the cost of the fixing member 180 can be reduced.

As a screw is unnecessary for fixing the fixing member 180 to the second frame 174, the screw tightening work accompanied by delicate torque control of the fixing member 180 becomes unnecessary. The assembly workability can be improved.

As the whole fixing member 180 is elastically held between the stopper lugs 174a and 174b of the second frame 174 made of a metallic material such as aluminum, a contacting area between parts is increased, and a strong contacting force is ensured. Therefore, thermal resistance between parts can be reduced, and thermal conductivity from the LED 92a to the treatment device insertion port 80 can be improved.

As thermal resistance between parts is reduced, thermal conductivity between parts can be further increased by inserting a heat compound into a contacting area between parts.

In the first and second embodiments described herein, metallic materials are used in the first and second frames 172 and 174, branch part 76, connection tube 78, and treatment device insertion port 80. However, the materials are not limited to metal, as long as appropriate rigidity and thermal conductivity are ensured. For example, use of the same material as the fixing member 180 may be preferable.

In the first and second embodiments described herein, the fixing member 180 is solid and substantially cylindrical. However, other forms, such as a truncated cone are permitted, as long as the second frame 174 can closely contact the outside surface of the fixing member 180. For example, when a truncated cone is adopted, it is preferable to make the outer dimensions of the side of the grip part 36 close to the protection hood 38 smaller than the side close to the operation portion main body 32.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
 an insertion portion configured to be inserted into a subject;
 an operation portion which is connected to a proximal end of the insertion portion, and which includes a first outer casing outside of the operation portion, the first outer casing being held by a user;
 a light source provided in the operation portion;
 a heat transmission frame having good thermal conductivity and being at least partially electrically insulative, the heat transmission frame being provided with the light source in the operation portion, and being configured to transmit heat generated by the light source, and
 an external heat radiation part which is connected to the heat transmission frame, is at least partially exposed to the outside of the operation portion, and is configured to radiate the heat from the light source transmitted to the heat transmission frame to the outside of the operation portion
 wherein the heat transmission frame
 is intermediated in a heat transmission path of the heat generated by the light source, between the light source and the external heat radiation part, said heat transmission frame has good thermal conductivity, is configured to transmit the heat generated by the light source and is electrically insulative and configured to shut out electric flow from the external heat radiation part to the light source when electric energy is input to the external heat radiation part, said heat transmission frame is completely disposed into the first outer casing of the operation portion and constructed and located to prevent static electric charge from reaching the light source, and
 a further frame disposed on the heat transmission frame and having good thermal conductivity and configured to transmit the heat generated by the light source.

2. The endoscope according to claim 1, wherein the heat transmission frame includes a light source fixing member which is configured to accommodate the light source therein and configured to transmit the heat generated by the light source to the further frame.

3. The endoscope according to claim 2, wherein the whole of the light source fixing member has electrically insulation properties and covers the light source.

4. The endoscope according to claim 2, wherein the light source fixing member is disposed in the further frame and configured to transmit the heat from the light source to the further frame through the light source fixing member, and
 the further frame is connected to the external heat radiation part and configured to transmit the heat from the further frame to the external heat radiation part.

5. The endoscope according to claim 1, wherein
 the heat transmission frame is disposed in the further frame and configured to transmit the heat from the light source to the further frame through the heat transmission frame, and
 the further frame is connected to the external heat radiation part and configured to transmit the heat from the further frame to the external heat radiation part.

6. The endoscope according to claim 1, wherein the heat transmission frame includes an electrical insulating part to cover the light source with an electrical insulator.

7. The endoscope according to claim 1, further comprising a channel extending between the operation portion and a distal end of the insertion portion,
 wherein the external heat radiation part includes a mouthpiece forming an opening of the channel in the operation portion.

8. The endoscope according to claim 7, wherein a forceps plug having electrical insulation is attachable to and detachable from the mouthpiece of the external heat radiation part,
 the forceps plug includes:
   a substantially cylindrical second outer casing having an engaging part, the second outer casing attachable to and detachable from the external heat radiation part; and
   a valve which is provided in the second outer casing, and which is configured to interrupt flowing of fluid between the inside of the channel and the outside of the mouthpiece of the external heat radiation part, and
 clearance is provided between the second outer casing of the forceps plug and the mouthpiece of the external heat radiation part.

9. The endoscope according to claim 8, wherein an end portion of the second outer casing of the forceps plug close to the heat transmission frame is enlarged in a flare configuration with respect to the mouthpiece.

10. The endoscope according to claim 7, wherein
 the first outer casing of the operation portion is disposed on the outside of the heat transmission frame,
 the operation portion includes an extension which is provided on the first outer casing and on the outside of the heat transmission frame,
 the light source includes an LED, and
 the external heat radiation part includes the opening of the channel in the extension.

11. The endoscope according to claim 1, wherein
 the first outer casing of the operation portion is disposed on the outside of the further frame of the heat transmission frame, and
 space is provided between the further frame and the first outer casing.

12. The endoscope according to claim 1, wherein the heat transmission frame has aluminum nitride having electrical insulation properties and good thermal conductivity.

13. The endoscope according to claim 1, wherein the heat transmission frame is extended in the operation portion, from the side far from the light source to the side close to the light source with respect to the distal end of the insertion portion.

* * * * *